(12) United States Patent
Kim

(10) Patent No.: US 7,894,656 B2
(45) Date of Patent: Feb. 22, 2011

(54) METHOD AND APPARATUS FOR INSPECTING MANUAL DISPENSING TRAY OF AUTOMATIC MEDICINE PACKAGING MACHINE

(75) Inventor: Jun Ho Kim, Daegu (KR)

(73) Assignee: JVM Co., Ltd, Taegu (KR)

( * ) Notice: Subject to any disclaimer, the term of this patent is extended or adjusted under 35 U.S.C. 154(b) by 877 days.

(21) Appl. No.: 11/754,778

(22) Filed: May 29, 2007

(65) Prior Publication Data

US 2008/0149657 A1 Jun. 26, 2008

(30) Foreign Application Priority Data

Dec. 22, 2006 (KR) .................... 10-2006-0133152

(51) Int. Cl.
*G06K 9/00* (2006.01)
(52) U.S. Cl. .................................................. 382/141
(58) Field of Classification Search ................ 382/141; 348/86, 92; 700/143, 204
See application file for complete search history.

(56) References Cited

U.S. PATENT DOCUMENTS

| | | | |
|---|---|---|---|
| 169,935 A | 11/1875 | Whitman |
| 350,675 A | 10/1886 | Hathaway |
| 488,721 A | 12/1892 | Stempel |
| 1,121,804 A | 12/1914 | Coulson |
| 1,270,756 A | 6/1918 | Holmberg |
| 1,912,248 A | 5/1933 | Bateman et al. |
| 2,005,496 A | 6/1935 | Cleveland |
| 2,181,314 A | 11/1939 | Burns |
| 2,208,951 A | 7/1940 | Tamassy |
| 2,255,036 A | 9/1941 | Gedge |
| 2,449,139 A | 9/1948 | Posner |
| 2,710,712 A | 6/1955 | Friedman |
| 2,712,883 A | 7/1955 | Esposito et al. |
| 2,918,069 A | 12/1959 | Brown, Jr. et al. |
| 2,994,996 A | 8/1961 | Klar |
| 3,074,214 A | 1/1963 | Schneider et al. |
| 3,227,127 A | 1/1966 | Gayle |
| 3,263,857 A | 8/1966 | Krakauer et al. |
| 3,348,392 A | 10/1967 | Schreiber |
| 3,408,876 A | 11/1968 | Andrews |
| 3,410,452 A | 11/1968 | Igel et al. |
| 3,481,103 A | 12/1969 | Summerour |
| 3,546,849 A | 12/1970 | Zimmerman |
| 3,562,475 A | 2/1971 | Angelotti et al. |
| 3,604,559 A | 9/1971 | McCall et al. |
| 3,774,368 A | 11/1973 | Paprzycki et al. |
| 3,820,655 A | 6/1974 | La Tourette et al. |

(Continued)

FOREIGN PATENT DOCUMENTS

| GB | 2178397 | 2/1987 |
|---|---|---|
| JP | 9-175510 | 7/1997 |
| JP | 9-266940 | 10/1997 |

*Primary Examiner*—Daniel G Mariam
(74) *Attorney, Agent, or Firm*—John K. Park; Park Law Firm

(57) ABSTRACT

A method for inspecting manual dispensing tray of the automatic medicine packaging machine that stably inspects dispensing error of the manual dispensing tray due to manual dispensing by a pharmacist and that prevents the inferiority of packaging due to the dispensing error of the manual dispensing tray is disclosed. The method includes step of confirming manual dispensing; step of photographing tray; step of acquiring medication information; step of analyzing information equivalence; and step of displaying dispensing error.

14 Claims, 5 Drawing Sheets

U.S. PATENT DOCUMENTS

| | | |
|---|---|---|
| 3,830,419 A | 8/1974 | Lee |
| 3,842,569 A | 10/1974 | McClelland et al. |
| 3,850,780 A | 11/1974 | Crawford et al. |
| 3,861,651 A | 1/1975 | Takamura |
| 3,871,156 A | 3/1975 | Koenig et al. |
| 3,921,419 A | 11/1975 | Rosenkranz et al. |
| 3,990,209 A | 11/1976 | Eisenberg |
| 4,019,547 A | 4/1977 | Ross |
| 4,149,394 A | 4/1979 | Sornes |
| 4,209,211 A | 6/1980 | Alford |
| 4,244,158 A | 1/1981 | Nelham |
| 4,254,601 A | 3/1981 | Prager et al. |
| 4,267,942 A | 5/1981 | Wick, Jr. et al. |
| 4,382,527 A | 5/1983 | Lerner |
| 4,519,179 A | 5/1985 | Meier |
| 4,534,499 A | 8/1985 | Cox et al. |
| 4,572,376 A | 2/1986 | Wrennall |
| 4,664,289 A | 5/1987 | Shimizu et al. |
| 4,696,392 A | 9/1987 | Chisholm, Jr. |
| 4,771,912 A | 9/1988 | van Wingerden |
| 4,790,118 A | 12/1988 | Chilcoate |
| 4,790,421 A | 12/1988 | Gorges |
| 4,811,764 A | 3/1989 | McLaughlin |
| 4,903,861 A | 2/1990 | Yuyama |
| 4,915,259 A | 4/1990 | Guigan et al. |
| 4,922,682 A | 5/1990 | Tait et al. |
| 4,955,178 A | 9/1990 | Shroyer |
| 5,069,511 A | 12/1991 | Swets et al. |
| 5,097,652 A | 3/1992 | Inamura et al. |
| 5,219,095 A | 6/1993 | Shimizu et al. |
| 5,221,024 A | 6/1993 | Campbell |
| 5,318,430 A | 6/1994 | Ramm |
| 5,337,919 A | 8/1994 | Spaulding et al. |
| 5,348,061 A | 9/1994 | Riley et al. |
| 5,381,904 A | 1/1995 | Thurell |
| 5,383,559 A | 1/1995 | Toren |
| 5,413,245 A | 5/1995 | Wright |
| 5,441,165 A | 8/1995 | Kemp et al. |
| 5,459,983 A | 10/1995 | Sadek et al. |
| 5,481,855 A | 1/1996 | Yuyama |
| 5,487,289 A | 1/1996 | Otto, III et al. |
| 5,502,944 A | 4/1996 | Kraft et al. |
| 5,509,573 A | 4/1996 | Campoli |
| 5,522,525 A | 6/1996 | McLaughlin et al. |
| 5,575,465 A | 11/1996 | Auerbach et al. |
| 5,588,792 A | 12/1996 | Tiso |
| 5,599,015 A | 2/1997 | Shimizu et al. |
| 5,611,456 A | 3/1997 | Kasper |
| 5,626,219 A | 5/1997 | Deefholts et al. |
| 5,651,476 A | 7/1997 | Percy et al. |
| 5,660,305 A | 8/1997 | Lasher et al. |
| 5,667,096 A | 9/1997 | Wu |
| 5,671,592 A | 9/1997 | Yuyama et al. |
| 5,678,393 A | 10/1997 | Yuyama et al. |
| 5,709,063 A | 1/1998 | Yuyama et al. |
| 5,722,215 A | 3/1998 | Yuyama |
| 5,749,117 A | 5/1998 | Forsline |
| 5,765,606 A | 6/1998 | Takemasa et al. |
| 5,787,678 A | 8/1998 | Koike et al. |
| 5,797,248 A | 8/1998 | Hetherington et al. |
| 5,803,309 A | 9/1998 | Yuyama et al. |
| 5,819,500 A | 10/1998 | Haraguchi et al. |
| 5,839,257 A | 11/1998 | Soderstrom et al. |
| 5,852,911 A | 12/1998 | Yuyama et al. |
| 5,865,342 A | 2/1999 | Ito et al. |
| 5,875,610 A | 3/1999 | Yuyama et al. |
| 5,901,876 A | 5/1999 | Yuyama et al. |
| 5,927,546 A | 7/1999 | Yuyama et al. |
| 5,930,145 A | 7/1999 | Yuyama et al. |
| 5,944,057 A | 8/1999 | Pierce |
| 5,946,883 A | 9/1999 | Yuyama et al. |
| 5,963,453 A | 10/1999 | East |
| 5,964,374 A | 10/1999 | Yuyama et al. |
| 5,987,859 A | 11/1999 | Dreger |
| 6,012,602 A | 1/2000 | Yuyama et al. |
| 6,023,916 A | 2/2000 | Bouthiette |
| 6,029,683 A | 2/2000 | Moebs et al. |
| 6,050,064 A | 4/2000 | Yuyama et al. |
| 6,089,136 A | 7/2000 | Hinojosa et al. |
| 6,109,486 A | 8/2000 | Lee, Jr. et al. |
| 6,119,440 A | 9/2000 | Benner, Jr. et al. |
| 6,119,892 A | 9/2000 | Laurent et al. |
| 6,145,700 A | 11/2000 | Takahashi et al. |
| 6,164,038 A | 12/2000 | Kim |
| 6,170,229 B1 | 1/2001 | Kim |
| 6,170,230 B1 | 1/2001 | Chudy et al. |
| 6,170,699 B1 | 1/2001 | Kim |
| 6,179,205 B1 | 1/2001 | Sloan |
| 6,202,385 B1 | 3/2001 | Kim |
| 6,216,418 B1 | 4/2001 | Kim |
| 6,256,963 B1 | 7/2001 | Kim |
| 6,263,639 B1 | 7/2001 | Kim |
| 6,273,335 B1 | 8/2001 | Sloan |
| 6,308,494 B1 | 10/2001 | Yuyama et al. |
| 6,311,743 B1 | 11/2001 | Baroncini |
| 6,318,051 B1 | 11/2001 | Preiss |
| 6,349,848 B1 | 2/2002 | Uema et al. |
| 6,364,517 B1 | 4/2002 | Yuyama et al. |
| 6,367,232 B2 | 4/2002 | Kim |
| 6,394,308 B1 | 5/2002 | Yuyama et al. |
| 6,409,290 B1 | 6/2002 | Lin |
| 6,427,865 B1 | 8/2002 | Stillwell et al. |
| 6,449,921 B1 | 9/2002 | Kim |
| 6,457,611 B1 | 10/2002 | Koehler |
| 6,471,089 B2 | 10/2002 | Liff et al. |
| 6,471,090 B1 | 10/2002 | Inamura et al. |
| 6,478,185 B2 | 11/2002 | Kodama et al. |
| 6,481,180 B1 | 11/2002 | Takahashi et al. |
| 6,508,279 B2 | 1/2003 | Siegel et al. |
| 6,540,101 B1 | 4/2003 | Kim |
| 6,581,356 B2 | 6/2003 | Kim |
| 6,585,132 B2 | 7/2003 | Kim |
| 6,604,019 B2 | 8/2003 | Ahlin et al. |
| 6,611,733 B1 | 8/2003 | De La Huerga |
| 6,644,504 B2 | 11/2003 | Yuyama et al. |
| 6,647,702 B1 | 11/2003 | Kim |
| 6,722,167 B1 | 4/2004 | Hsu |
| 6,772,907 B2 | 8/2004 | Kim |
| 6,786,356 B2 | 9/2004 | Geiger et al. |
| 6,792,736 B1 | 9/2004 | Takahashi |
| 6,805,259 B2 | 10/2004 | Stevens et al. |
| 6,898,919 B2 | 5/2005 | Kim |
| 7,028,447 B2 | 4/2006 | Sung |
| 7,059,098 B2 | 6/2006 | Kim |
| 7,331,151 B2 | 2/2008 | Kim |
| 2002/0092275 A1 | 7/2002 | Kim |
| 2003/0057225 A1 | 3/2003 | Kim |
| 2003/0074868 A1 | 4/2003 | Yasuoka et al. |
| 2004/0046020 A1 | 3/2004 | Andreasson et al. |
| 2004/0129716 A1 | 7/2004 | Naufel et al. |
| 2004/0182044 A1 | 9/2004 | Kim |
| 2005/0179349 A1 | 8/2005 | Booth et al. |
| 2005/0234430 A1 | 10/2005 | Mao et al. |
| 2006/0058918 A1 | 3/2006 | Handfield et al. |
| 2006/0070352 A1 | 4/2006 | Momich |
| 2006/0139148 A1 | 6/2006 | Faro et al. |
| 2006/0267727 A1 | 11/2006 | Cayne et al. |
| 2006/0273106 A1 | 12/2006 | Kim |
| 2007/0016327 A1 | 1/2007 | Yuyama et al. |
| 2007/0078562 A1 | 4/2007 | Park |
| 2007/0125100 A1 | 6/2007 | Shoenfeld |
| 2007/0151204 A1 | 7/2007 | Kim |
| 2007/0208595 A1 | 9/2007 | Ohmura et al. |
| 2007/0257773 A1 | 11/2007 | Hill et al. |

METHOD AND APPARATUS FOR INSPECTING MANUAL DISPENSING TRAY OF AUTOMATIC MEDICINE PACKAGING MACHINE

CLAIMING FOREIGN PRIORITY

The applicant claims and requests a foreign priority, through the Paris Convention for the Protection of Industrial Property, based on patent applications filed in the Republic of Korea (South Korea) with the filing date of Dec. 22, 2006, with the patent application number 10-2006-0133152 by the applicant, the contents of which are incorporated by reference into this disclosure as if fully set forth herein.

BACKGROUND OF THE INVENTION

The present invention relates to an automatic medicine packaging machine that packages each dose of medication. Specifically, the present invention relates to method and apparatus for inspecting manual dispensing tray of the automatic medicine packaging machine that stably inspect dispensing error of the manual dispensing tray due to manual dispensing by a pharmacist and that prevent the inferiority of packaging due to the dispensing error of the manual dispensing tray.

In general, an automatic medicine packaging machine continuously packages tablet-type medications that are dispensed per dose. The construction and operation of an automatic medicine packaging machine are explained as follows referring to FIG. 3, FIG. 4, and FIG. 5: the automatic medicine packaging machine includes a body 100 having a plurality of tablet cassettes 101 that is built on a shelf in the upper part of the machine, a tablet dispenser 200 inside the body 100, a hopper 300 that is constructed below the tablet cassettes 101 and the tablet dispenser 200, a printing unit 400, and a sealing unit 500 that feeds and seals medication envelopes on which instruction labels are printed by the printing unit 400.

The operation of the tablet cassettes 101, the printing unit 400, and the sealing unit 500 are controlled by a controller C that is installed inside the body 100. The controller C operates to make a package of each dose of medication by controlling the tablet cassettes 101, the printing unit 400, and the sealing unit 500 according to prescription data inputted from a computer server S.

A manual dispensing tray 201 which is installed in the upper part of the tablet dispenser 200 has a plurality of compartments to which medications may be dispensed, and it can be operated to be ejected from the front of the body 100. To each compartment, manual dispensing is made by a pharmacist for tablets which are hard to be provided automatically because they are not housed in the tablet cassettes 101 or for half-tablets which are hard to be supplied by the tablet cassettes 101.

A pharmacist manually compounds prescription medications by dispensing to each compartment while the manual dispensing tray 201 is in the state of being pulled out from the front of the body 100. When the manual dispensing is finished, medications will be fallen into the tablet dispenser 200 after residing inside the body 100 and be discharged to the hopper 300 automatically.

However, the above prior art has a disadvantage as follows: manual dispensing is done by a pharmacist, so that it is hard to inspect dispensing error due to wrong dispensing. In addition, it gives rise to the inferiority of packaging due to the dispensing error of the manual dispensing tray.

SUMMARY OF THE INVENTION

The present invention contrives to solve the above disadvantage of the prior art.

An objective of the invention is to provide method and apparatus for inspecting manual dispensing tray of an automatic medicine packaging machine that stably inspect dispensing error of the manual dispensing tray due to manual dispensing by a pharmacist and that prevent the inferiority of packaging due to the dispensing error of the manual dispensing tray.

Another objective of the invention is to provide method and apparatus of the automatic medicine packaging machine that, when the dispensing error is occurred, dissolve the dispensing error and make a pharmacist recognize it promptly.

In order to accomplish the above objectives of the invention, a method for inspecting manual dispensing tray of an automatic medicine packaging machine based on a preferred embodiment includes step of confirming manual dispensing, in which, after a manual dispensing tray is drawn from a body of an automatic medicine packaging machine, by detecting the manual dispensing tray's being received back into the interior of the body, manual dispensing of medications onto the manual dispensing tray is confirmed; step of photographing tray, in which, when the manual dispensing of medications onto the manual dispensing tray is confirmed, state of the manual dispensing of medications onto the manual dispensing tray is acquired as images by photographing the top view of the manual dispensing tray; step of acquiring medication information, in which information on medications that are dispensed on each compartment of the manual dispensing tray is acquired by analyzing the images obtained from photographing the manual dispensing tray; and step of analyzing information equivalence, in which equivalence between the medication information obtained from the image analysis and manual prescription information extracted from prescription data inputted from a server computer is analyzed.

In the step of acquiring medication information the image analysis is to acquire information on kind and number of medications by comparing and analyzing shapes and colors of medications extracted from the images obtained from photographing the manual dispensing tray and those of medications extracted from medication shape information which is stored in advance.

In the step of analyzing information equivalence, if the medication information and the manual prescription information are mutually equivalent, then the process proceeds to step of compounding prescription, in which medications are compounded as prescribed, but if they are mutually inequivalent, then the process proceeds to step displaying dispensing error, in which dispensing error due to manual dispensing is displayed according to the analysis of the information equivalence.

The method further includes step of re-dispensing medication after the step of displaying dispensing error, in which each compartment of the manual dispensing tray that has mutually inequivalent information is displayed and the manual dispensing tray outside the body of the automatic medicine packaging machine is ejected for re-dispensing medications.

The method further included step of acquiring number of compartments after the step of photographing the tray, in which number of compartments of the manual dispensing tray that medications are dispensed is acquired by analyzing the images obtained from photographing the manual dispensing tray.

The method further includes step of analyzing dispensing number equality after the step of photographing tray, in which equality between number of compartments of the manual dispensing tray that medications are dispensed and number of compartments of the manual dispensing tray that medications will be dispensed is analyzed, in which the latter number is extracted from the prescription data inputted from the server computer.

In the step of analyzing dispensing number equality, in which, if the number of compartments of the manual dispensing tray that medications are dispensed and the number of compartments that medications will be dispensed are mutually equal, then the process proceeds to the step of acquiring medication information, but if they are mutually unequal, then the process proceeds to step of displaying dispensing number error, in which dispensing number error due to manual dispensing is displayed according to the analysis of the dispensing number equality.

The method further includes step of dissolving inequality after the step of displaying dispensing number error, in which the mutually unequal numbers of compartments of the manual dispensing tray are displayed, and also the manual dispensing tray is ejected outside the body of the automatic medicine packaging machine for re-dispensing medications.

The invention also provides an apparatus for inspecting manual dispensing tray of an automatic medicine packaging machine based on a preferred embodiment includes a manual dispensing tray that can be operated to be injected and ejected from a body of the automatic medication packaging machine; a camera that acquires the state of the manual dispensing medications onto the manual dispensing tray as images by photographing the top view of the manual dispensing tray; a shape information storage unit that stores shapes and colors of each medication that will be dispensed onto the manual dispensing tray; an image analysis unit that acquires information on medications which are dispensed on each compartment of the manual dispensing tray by comparing and analyzing shapes and colors of medications extracted from the images photographed by the camera and those of medications extracted from the shape information storage unit; and a controller that inspects whether a pharmacist has precisely dispensed medications to the manual dispensing tray by analyzing equivalence between medication information obtained from the image analysis unit, and manual prescription information extracted from prescription data inputted from a server computer.

The apparatus further includes a display which displays inequivalent state if the information on medications dispensed to the manual dispensing tray is inequivalent to the manual dispensing information according to the analysis of the controller.

The image analysis unit extracts number of such compartments of the manual dispensing tray that medications are dispensed, in which the number is extracted by analyzing the images obtained from photographing the manual dispensing tray by the camera.

The controller analyzes equality between number of compartments of the manual dispensing tray extracted from the image analysis unit and number of compartments that medications will be dispensed, in which the latter number is extracted from the prescription data inputted from the server computer.

The display displays dispensing number error if the number of compartments of the manual dispensing tray extracted from the image analysis unit and the number of compartments extracted from the prescription data are mutually unequal according to the analysis of the controller.

The controller operates to make the manual dispensing tray to be ejected outside the body of automatic medicine packaging machine by controlling the manual dispensing tray if the number of compartments extracted from the image analysis unit is unequal to the one from the prescription data or if the medication information extracted from the image analysis unit is inequivalent to the one from prescription data.

The present invention has an advantageous effect that stably inspects dispensing error of the manual dispensing tray due to manual dispensing by a pharmacist and that prevents the inferiority of packaging due to the dispensing error of the manual dispensing tray.

Another Advantageous effect of the invention is to dissolve the dispensing error, make a pharmacist recognize it, and promptly do a subsequent action, such as re-dispense of medications, when the dispensing error is occurred.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENT

Figure 1:
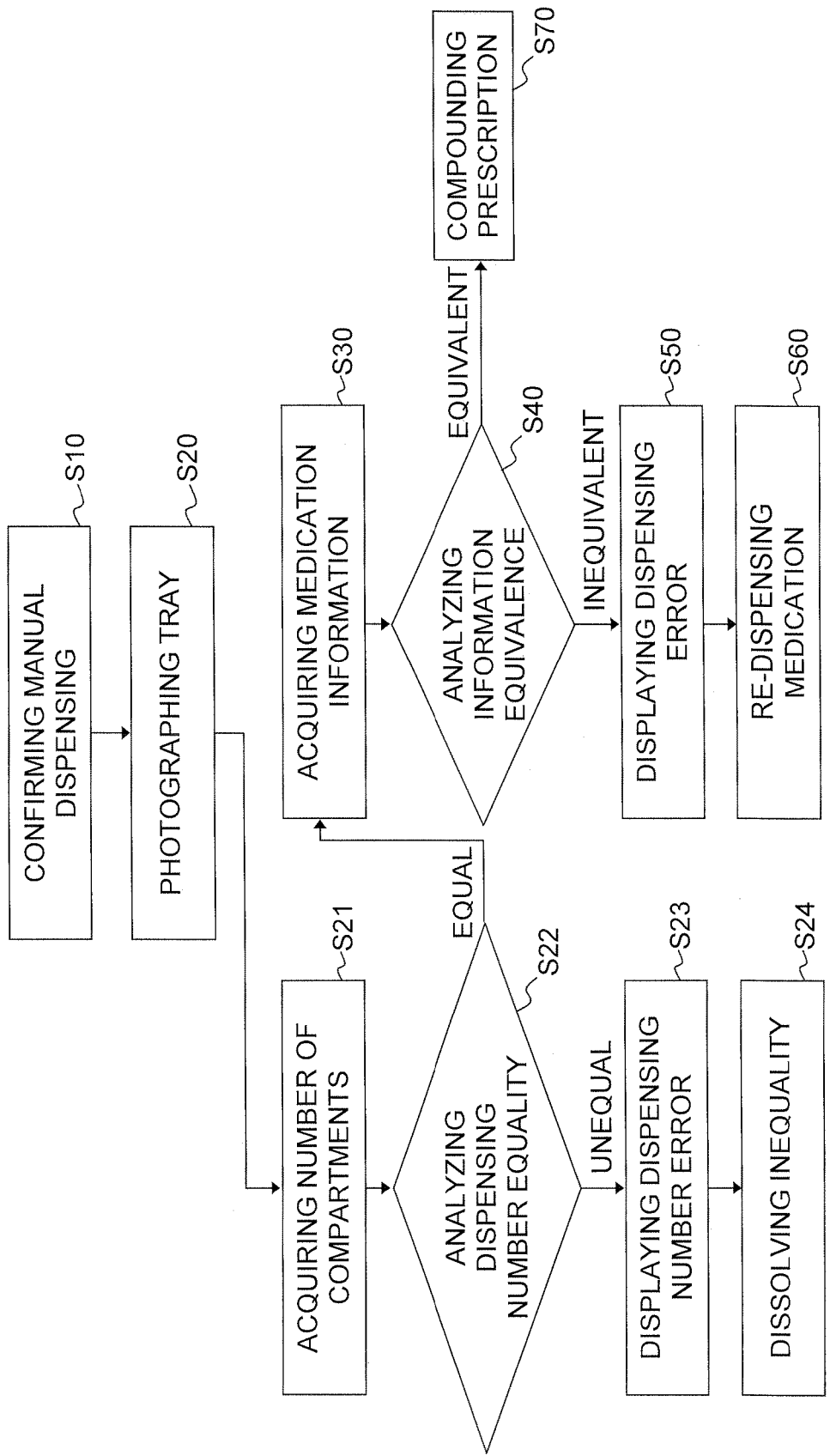
FIG. 1 is a flow diagram of a method for inspecting manual dispensing tray of an automatic medicine packaging machine according to the present invention.

Referring to FIG. 1, a method for inspecting a manual dispensing tray of an automatic medicine packaging machine includes step S10 of confirming manual dispensing, in which manual dispensing to the manual dispensing tray is confirmed; step S20 of photographing tray, in which, after the manual dispensing is confirmed, the manual dispensing tray is photographed; step S30 of acquiring medication information, in which medication information is acquired from the photographed images; and step S40 of analyzing information equivalence, in which equivalence between the medication information and manual prescription information extracted from prescription data is analyzed.

In the step S10 of confirming manual dispensing, after the manual dispensing tray is drawn from a body of the automatic medicine packaging machine, by detecting the manual dispensing tray's being received back into the interior of the body, manual dispensing of medications onto the manual dispensing tray is confirmed. In other words, when the manual dispensing tray is ejected from the body and then inserted again, the appropriate timing of photographing the manual dispensing tray may be recognized by detecting the manual dispensing of medications onto the manual dispensing tray by a pharmacist.

In the step S20 of photographing tray, when the manual dispensing of medications onto the manual dispensing tray is confirmed, state of the manual dispensing of medications onto the manual dispensing tray is acquired as images by photographing the top view of the manual dispensing tray. In other words, images of the medications which are dispensed onto each compartment of the manual dispensing tray are acquired.

In the step S30 of acquiring medication information, information on medications that are dispensed on each compartment of the manual dispensing tray is acquired by analyzing the images obtained from photographing the manual dispensing tray. The image analysis is to acquire information on kind and number of medications by comparing and analyzing shapes and colors of medications extracted from the images obtained from photographing the manual dispensing tray and those of medications extracted from medication shape information which is stored in advance.

In the step S40 of analyzing information equivalence, equivalence between the medication information acquired from the image analysis and manual prescription information extracted from prescription data inputted from a server computer is analyzed. That is, in this step analyzed is the information equivalence between the information on medications which are manually dispensed on each compartment of the manual dispensing tray and the manual prescription information on medications which are extracted from the prescription data and are to be prescription compounded. If the medication information and the manual prescription information are mutually equivalent, then the process proceeds to step S70 of compounding medications, but if they are mutually inequivalent, then the process proceeds to step S50 of displaying dispensing error according to the analysis of information equivalence. In other words, if the medication information is equivalent to the manual prescription information, then the process proceeds to step S70 of compounding medications because a pharmacist has dispensed medications precisely to the manual dispensing tray according to the manual prescription information, but on the other hand if they are mutually inequivalent, then the process proceeds to step S50 of displaying dispensing error.

In the step S50 of displaying dispensing error after the step S40 of information equivalence, dispensing error due to manual dispensing is displayed. The process stops dispensing because a pharmacist has dispensed imprecisely.

The method further includes step S60 of medication re-dispensing after the step S50 of displaying dispensing error, in which each compartment of the manual dispensing tray that has mutually inequivalent information is displayed, and the manual dispensing tray outside the body of the automatic medicine packaging machine is ejected for re-dispensing medications. This step makes a pharmacist to re-dispense medications dispensed in compartments that manual dispensing is imprecise.

In the step S70 of compounding prescription after the step S40 of information equivalence, medications are compounded as prescribed.

The method for inspecting the manual dispensing tray of the automatic medication packaging machine further includes step S21 of acquiring number of compartments after the step S20 of photographing tray, in which number of compartments of the manual dispensing tray that medications are dispensed is acquired by analyzing the images obtained from photographing the manual dispensing tray; step S22 of analyzing dispensing number equality, in which equality between the number of compartments of the manual dispensing tray that medications are dispensed and number of compartments extracted from the prescription data is analyzed; step S23 of displaying dispensing number error, in which dispensing number error due to manual dispensing is displayed; and step S24 of dissolving inequality via re-dispensing medications.

In the step S21 of acquiring number of compartments, in which number of compartments of the manual dispensing tray that medications are dispensed is acquired by analyzing the images obtained from photographing the manual dispensing tray In the step S22 of analyzing dispensing number equality after the step S21 of acquiring number of compartments, equality between the number of compartments of the manual dispensing tray that medications are dispensed and number of compartments of the manual dispensing tray that medications will be dispensed is analyzed, in which the latter number is extracted from the prescription data inputted from the server computer is analyzed. This step will be performed before the step S40 of analyzing information equivalence. If the number of compartments of the manual dispensing tray that medications are dispensed and the number of compartments of the manual dispensing tray that medications will be dispensed are mutually equal, then the process proceeds to the step S40 of acquiring medication information, but if they are mutually unequal, then the process proceeds to the step S23.

In the step S23 of displaying dispensing number error after the step S22 of analyzing dispensing number equality, dispensing number error due to the manual dispensing is displayed according to the analysis of the dispensing number equality. This makes a pharmacist to recognize the dispensing number error, to be exact, the error occurs when the number of compartments is either plethora or shortage.

In the step S24 of dissolving inequality after the step S23 of displaying dispensing number error, the mutually unequal number of compartments of the manual dispensing tray is displayed, and also the manual dispensing tray is ejected outside the body of the automatic medicine packaging machine for re-dispensing medications. This step makes a pharmacist to re-dispense medications dispensed in compartments that the manual dispensing is imprecise.

Figure 2:
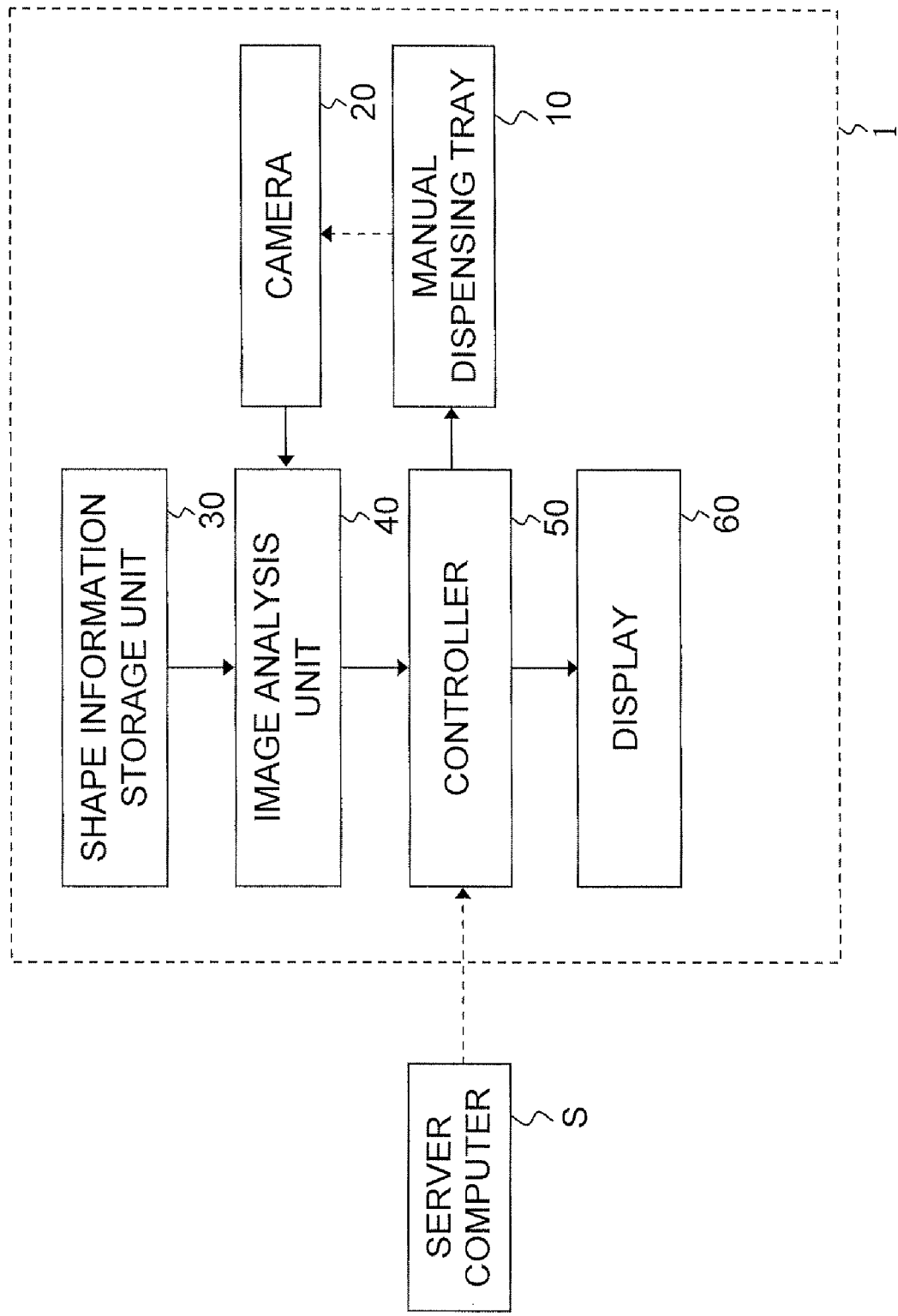
FIG. 2 is a block diagram of an apparatus for inspecting manual dispensing tray of an automatic medicine packaging machine according to the present invention.
Figure 3:
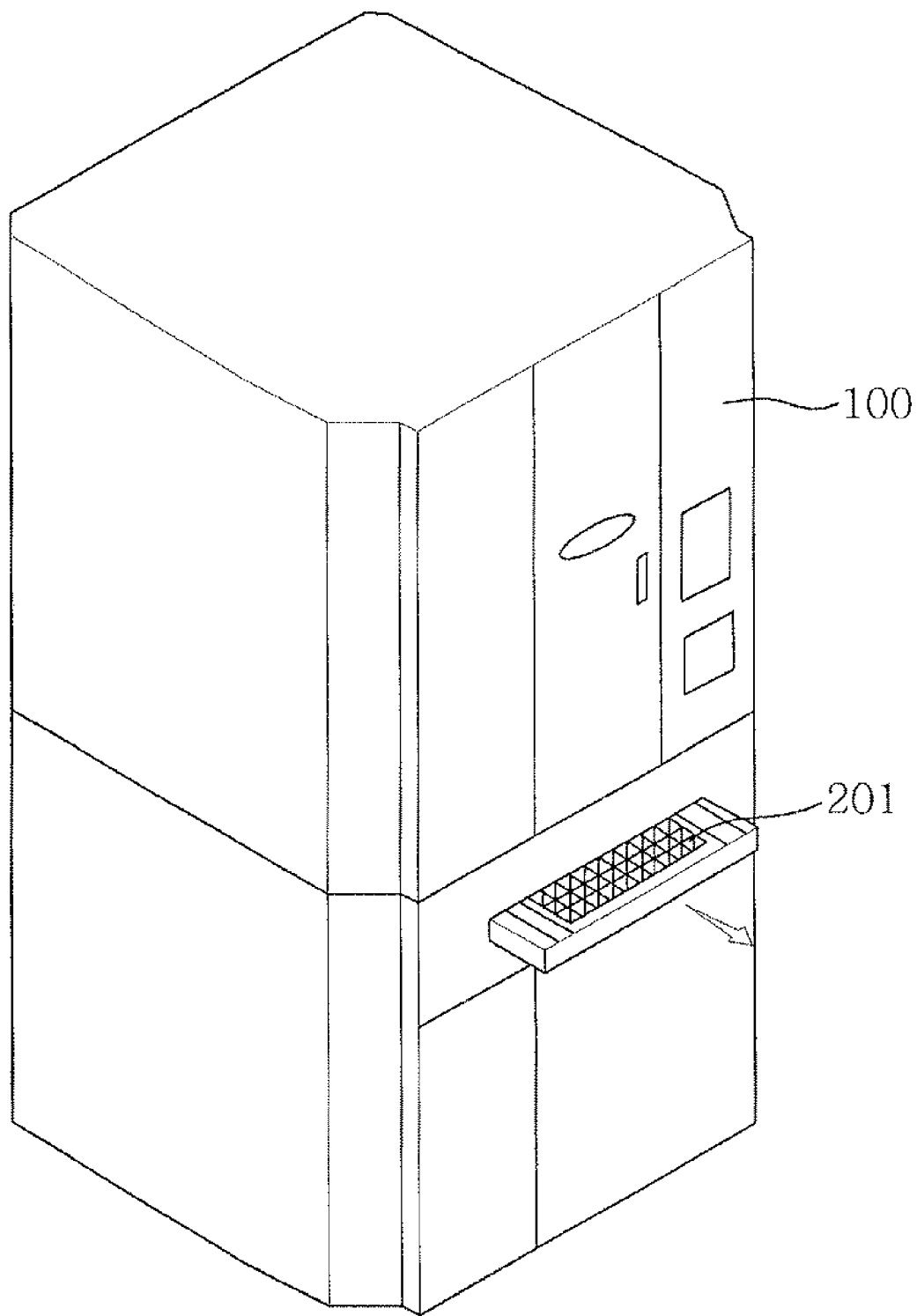
FIG. 3 is a perspective view of an automatic medicine packaging machine.
Figure 4:
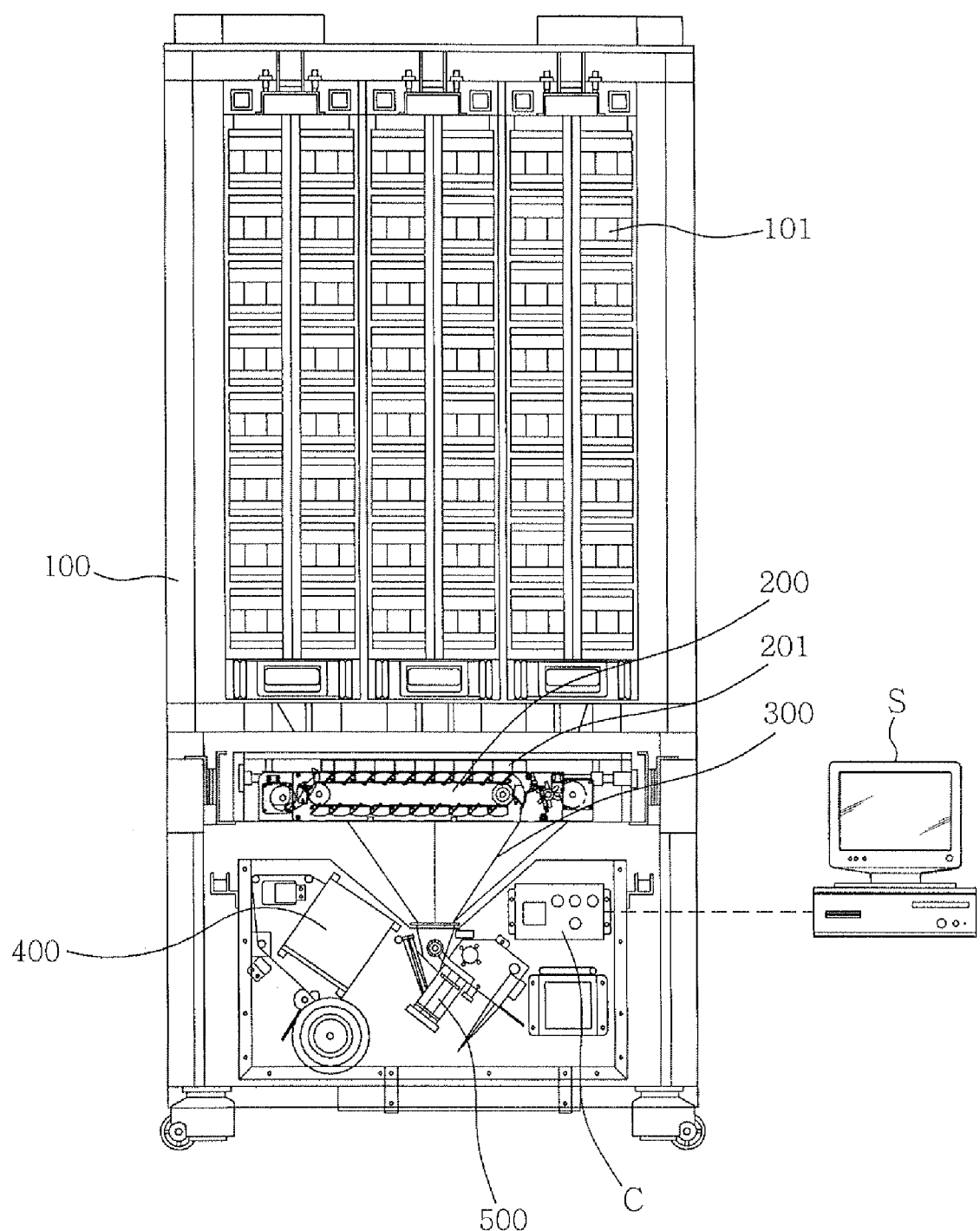
FIG. 4 is an elevation view of an automatic medicine packaging machine.
Figure 5:
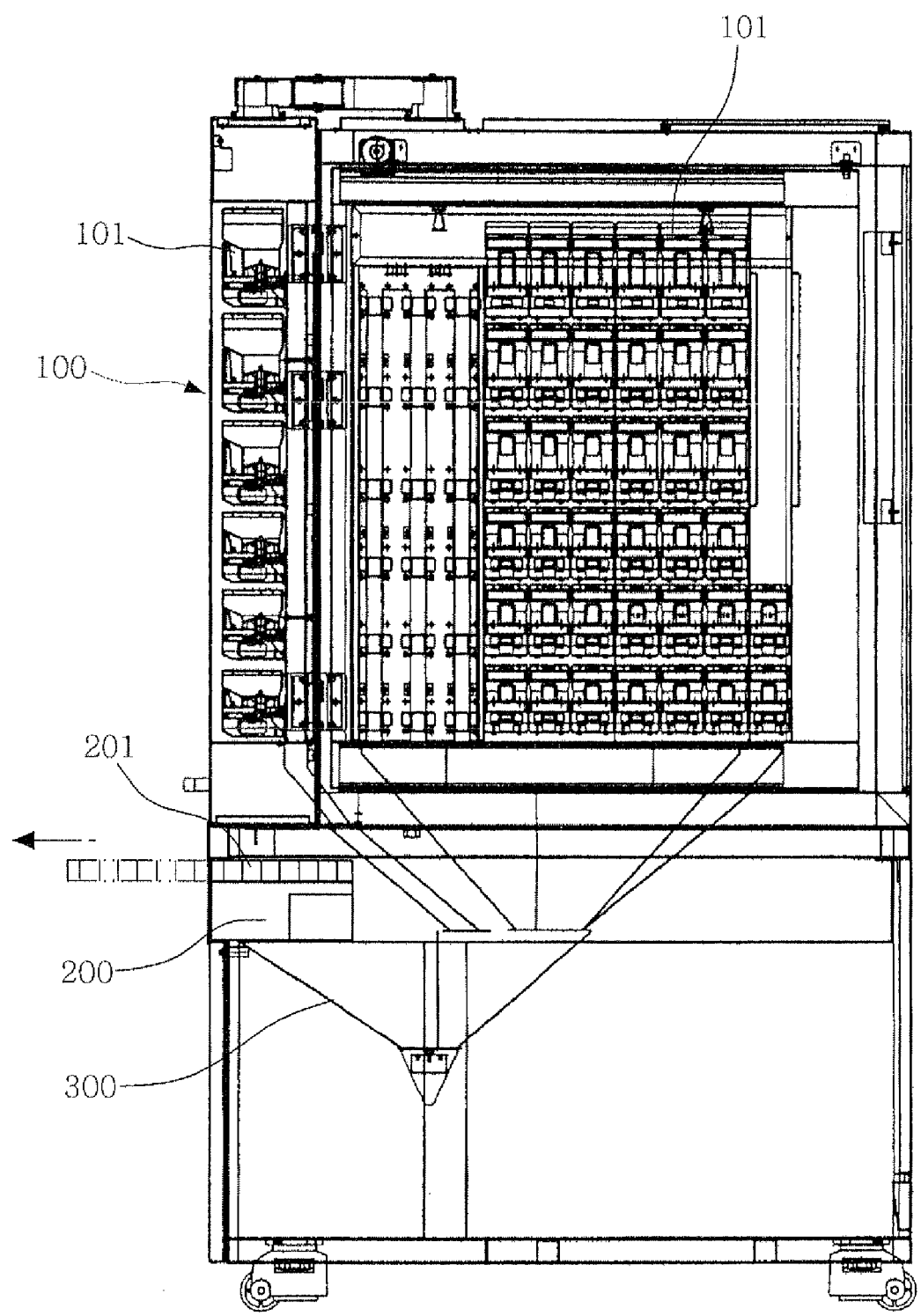
FIG. 5 is an elevation view of an automatic medicine packaging machine.

Referring to FIG. 2, an apparatus for inspecting a manual dispensing tray of an automatic medication packaging machine includes a manual dispensing tray 10 that is established in the body of the automatic medication packaging machine 1; a camera 20 that photographs the top view of the manual dispensing tray 10; a shape information storage unit 30 that stores shapes and colors of medications; an image analysis unit 40 that analyzes images obtained from photographing; and a controller 50 that compares and analyzes information inputted from the image analysis unit 40 with information extracted from prescription data.

The manual dispensing tray 10 has an array of a plurality of compartments, in which medications will be manually dispensed, and can be operated to be injected and ejected from the front of the body of the automatic medication packaging machine 1. Manual dispensing is made to each compartment by a pharmacist.

The camera 20 acquires, after the manual dispensing of medications onto the manual dispensing tray 10 is confirmed, state of the manual dispensing of medications onto the manual dispensing tray 10 as images by photographing the top view of the manual dispensing tray 10.

The shape information storage unit 30 stores information on shapes and colors of each medication that will be dispensed onto the manual dispensing tray 10.

The image analysis unit 40 acquires information on medications which are dispensed on each compartment of the manual dispensing tray 10 by comparing and analyzing shapes and colors of medications extracted from the images photographed by the camera 20 and those of medications extracted from the shape information storage unit 30.

The controller 50 inspects whether a pharmacist has precisely dispensed medications to the manual dispensing tray 10 by analyzing equivalence between medication information obtained from the image analysis unit 40 and manual prescription information extracted from prescription data inputted from a server computer S.

The apparatus further includes a display 60 which displays inequivalent state if the information on medications dispensed to the manual dispensing tray 10 is inequivalent to the manual dispensing information according to the analysis of the controller 50. The display 60, which is connected to the controller 50, is established on a side of the automatic medication packaging machine 1 and displays the inequivalent state of the manual dispensing tray 10 while being controlled by the controller 50.

The image analysis unit 40 extracts number of compartments of the manual dispensing tray that medications are dispensed, in which the number is extracted by analyzing the images obtained from photographing the manual dispensing tray by the camera 20.

The controller 50 analyzes equality between the number of compartments extracted from the image analysis unit 40 and number of compartments of the manual dispensing tray that medications will be dispensed, in which the latter number is extracted from the prescription data inputted from the server computer S.

The display 60 indicates dispensing error if the number of compartments of the manual dispensing tray extracted from the image analysis unit and the number of compartments extracted from the prescription data are mutually unequal according to the analysis of the controller.

The controller 50 operates to make the manual dispensing tray 10 to be ejected outside the body of automatic medicine packaging machine by controlling the manual dispensing tray 10 if the number of compartments extracted from the image analysis unit 40 is unequal to the one from the prescription data or if the medication information extracted from the image analysis unit 40 is inequivalent to the one from the prescription data. This step dissolves the dispensing error via a pharmacist's re-dispensing medications onto the manual dispensing tray 10.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A method for inspecting manual dispensing tray of an automatic medicine packaging machine including steps of:
   a) confirming manual dispensing, wherein, after a manual dispensing tray is drawn from a body of an automatic medicine packaging machine, by detecting the manual dispensing tray's being received back into the interior of the body, manual dispensing of medications onto the manual dispensing tray is confirmed;
   b) photographing tray, wherein, when the manual dispensing of medications onto the manual dispensing tray is confirmed, state of the manual dispensing of medications onto the manual dispensing tray is acquired as images by photographing the top view of the manual dispensing tray;
   c) acquiring medication information, wherein information on medications that are dispensed on each compartment of the manual dispensing tray is acquired by analyzing the images obtained from photographing the manual dispensing tray; and
   d) analyzing information equivalence, wherein equivalence between the medication information obtained from the image analysis and manual prescription information extracted from prescription data inputted from a server computer is analyzed.

2. The method of claim 1, wherein in the step of acquiring medication information, the image analysis is to acquire information on kind and number of medications by comparing and analyzing shapes and colors of medications extracted from the images obtained from photographing the manual dispensing tray and those of medications extracted from medication shape information which is stored in advance.

3. The method of claim 1, wherein in the step of analyzing information equivalence, if the medication information and the manual prescription information are mutually equivalent, then the process proceeds to step of compounding prescription, wherein medications are compounded as prescribed, but if they are mutually inequivalent, then the process proceeds to step of displaying dispensing error, wherein dispensing error due to manual dispensing is displayed according to the analysis of the information equivalence.

4. The method of claim 3, further comprising step of re-dispensing medication after the step of displaying dispensing error, wherein each compartment of the manual dispensing tray that has mutually inequivalent information is displayed, and the manual dispensing tray outside the body of the automatic medicine packaging machine is ejected for re-dispensing medications.

5. The method of claim 1, further comprising step of acquiring number of compartments after the step of photographing tray, wherein number of compartments of the manual dispensing tray that medications are dispensed is acquired by analyzing the images obtained from photographing the manual dispensing tray.

6. The method of claim 5, further comprising step of analyzing dispensing number equality after the step of acquiring number of compartments, wherein equality between the number of compartments of the manual dispensing tray that medications are dispensed and number of compartments that medications will be dispensed is analyzed, in which the latter number is extracted from the prescription data inputted from the server computer.

7. The method of claim 6, in the step of analyzing dispensing number equality, wherein, if the number of compartments of the manual dispensing tray that medications are dispensed and the number of compartments that medications will be dispensed are mutually equal, then the process proceeds to the step of acquiring medication information, but if they are mutually unequal, then the process proceeds to step of displaying dispensing number error, wherein dispensing number error due to manual dispensing is displayed according to the analysis of the dispensing number equality.

8. The method of claim 7, further comprising step of dissolving inequality after the step of displaying dispensing number error, wherein the mutually unequal numbers of compartments of the manual dispensing tray are displayed, and also the manual dispensing tray is ejected outside the body of the automatic medicine packaging machine for re-dispensing medications.

9. An apparatus for inspecting manual dispensing tray of an automatic medicine packaging machine based on a preferred embodiment comprising:
   a) a manual dispensing tray that can be operated to be injected and ejected from a body of the automatic medication packaging machine;
   b) a camera that acquires state of the manual dispensing medications onto the manual dispensing tray as images by photographing the top view of the manual dispensing tray;

c) a shape information storage unit that stores shapes and colors of each medication that will be dispensed onto the manual dispensing tray;

d) an image analysis unit that acquires information on medications which are dispensed on each compartment of the manual dispensing tray by comparing and analyzing shapes and colors of medications extracted from the images photographed by the camera and those of medications extracted from the shape information storage unit; and e) a controller that inspect whether a pharmacist has precisely dispensed medications to the manual dispensing tray by analyzing equivalence between medication information obtained from the image analysis unit, and manual prescription information extracted from prescription data inputted from a server computer.

10. The apparatus of claim 9, further comprising a display which displays inequivalent state if the information on medications dispensed to the manual dispensing tray is inequivalent to the manual dispensing information according to the analysis of the controller.

11. The apparatus of claim 9, wherein the image analysis unit extracts number of compartments of the manual dispensing tray that medications are dispensed, in which the number is extracted by analyzing the images obtained from photographing the manual dispensing tray by the camera.

12. The apparatus of claim 11, wherein the controller analyzes equality between the number of compartments of the manual dispensing tray extracted from the image analysis unit and number of compartments that medications will be dispensed, in which the latter number is extracted from the prescription data inputted from the server computer.

13. The apparatus of claim 12, wherein the display displays dispensing number error if the number of compartments of the manual dispensing tray extracted from the image analysis unit and the number of compartments extracted from the prescription data are mutually unequal according to the analysis of the controller.

14. The apparatus of claim 12, wherein the controller operates to make the manual dispensing tray to be ejected outside the body of automatic medicine packaging machine by controlling the manual dispensing tray if the number of compartments extracted from the image analysis unit is unequal to the one from the prescription data or if the medication information extracted from the image analysis unit is inequivalent to the one from the prescription data.

* * * * *